United States Patent [19]

Wright et al.

[11] Patent Number: 4,793,354

[45] Date of Patent: * Dec. 27, 1988

[54] TOUCH ENHANCEMENT

[75] Inventors: H. Earl Wright; Don A. Perry, both of Decatur, Ill.

[73] Assignee: Inventive Products, Inc., Decatur, Ill.

[ * ] Notice: The portion of the term of this patent subsequent to Apr. 14, 2004 has been disclaimed.

[21] Appl. No.: 110,379

[22] Filed: Oct. 20, 1987

[51] Int. Cl.$^4$ ................................................ A61B 5/00
[52] U.S. Cl. ...................................... 128/630; 434/113
[58] Field of Search ...................... 128/1 R, 67, 138 R, 128/630, 744; 604/346, 349; 383/118, 3; 2/163, 168, DIG. 7; 434/113, 267

[56] References Cited

U.S. PATENT DOCUMENTS

| 2,694,396 | 11/1954 | Paschal | 128/67 |
| 3,633,216 | 1/1972 | Schonholtz | 2/168 |
| 4,657,021 | 4/1987 | Perry et al. | 128/630 |

*Primary Examiner*—Edward M. Coven
*Assistant Examiner*—Randy Citrin
*Attorney, Agent, or Firm*—Samuels, Miller, Schroeder, Jackson & Sly

[57] ABSTRACT

The sense of touch is enhanced by: (1) placing two layers of a pliable, elastic material between the fingertips and the object being touched; (2) maintaining the coefficient of kinetic friction between the two layers at less than the coefficient between the fingertips and the top layer and less than the coefficient between the object being touched and the bottom layer; and (3) moving the fingertips over the object being touched separated by the two layers of material.

5 Claims, No Drawings

TOUCH ENHANCEMENT

FIELD OF THE INVENTION

This invention relates to touch enhancement. More particularly, this invention relates to a method of enhancing the sense of touch.

BACKGROUND OF THE INVENTION

The sense of touch is one of the five senses by which we gather information about the world around us. The sense of touch gives rise to feelings of pleasure and pain and is used to determine the shape, hardness, texture, and temperature of objects. The sense of touch has special importance in situations where the sense of sight cannot be used. For example, the sense of touch is used by the blind for a variety of purposes, including reading with braille. The sense of touch is also used extensively in the field of medicine because the shape and hardness of internal body parts (which are hidden from sight under a layer of skin) are often an excellent guide in diagnosing and treating disease.

One of the most publicized uses of the sense of touch in medical diagnosis is the detection of breast cancer. One out of every eleven women in the United States develops breast cancer. It is the most common form of cancer in women and is the chief cause of cancer deaths among United States women. Breast cancer is characterized by the formation of lumps in the breast and early detection of the lumps is considered extremely important in treating the disease. Breast lumps can be detected by X-ray radiation photography or by manual examination. The known tendency of X-ray radiation to cause various types of cancer generally prevents its routine use for detection. Accordingly, most breast cancers are discovered by the detection of lumps by physical examination of the breasts. Manual examination of the breasts is included by most physicians in their routine examinations of women. To help with early detection, the American Cancer Society also recommends monthly self-examinations for women.

To reduce friction and thereby facilitate movement of the hands across the breasts, the American Cancer Society recommends that the monthly self-examinations be conducted during a bath or shower when the skin is wet and soapy. For any number of reasons, many women find it inconvenient to take the additional time for self-examination during their bath or shower. And, for obvious reasons, it is not practical to use water and/or soap as a skin lubricant for breast examination when partially clothed, e.g., at a physician's office. Creams, powders, or lotions are more suitable as friction reducers, but still are rarely used because of the mess. Therefore, most physicians and women conduct breast examinations by using their hands directly on dry skin.

Unfortunately, manual examination of the breasts does not ensure that a lump will be detected. In an article entitled "Physicians' Abilities to Detect Lumps in Silicone Breast Models" published in the Apr. 19, 1985 issue of the *Journal of The American Cancer Society*, (Vol. 253, No. 15, pp. 2224–2228), Dr. Suzanne W. Fletcher et al. of the University of North Carolina at Chapel Hill described a study which tested the ability of 80 physicians to detect lumps of varying sizes, hardness, and depth in silicone breast models. Dr. Fletcher et al. found that the physicians were able to detect only 44 percent of the lumps.

It is not difficult to understand why the detection results were so poor in the study. When conducting a breast cancer examination with bare hands on dry skin, the examiner must ignore the unwanted touch stimuli (i.e., the "noise", e.g., temperature, texture, and, if a self-examination, stimuli from the breast itself) in favor of the desired touch stimuli which enable the determination of shape and hardness of an object (i.e., the "signal"). The sense of touch is clearly an ability which can be developed with practice. For example, thousands of blind persons are able to read braille lettering, but a sighted person touching braille for the first time is usually unable to distinguish the number or pattern of the protrusions. Consequently, Dr. Fletcher et al. recommended more training for physicians to better develop their senses of touch.

Perry, et al., U.S. Pat. No. 4,657,021, issued Apr. 14, 1987, which is incorporated by reference, discloses a touch enhancing pad and a method of using the pad to enhance the sense of touch. The pad, as claimed, comprises a sealed enclosure of a single piece of pliable, elastic material and a liquid lubricant inside the enclosure in an amount sufficient to fully coat the interior of the enclosure, provided that the amount of the liquid lubricant permits the enclosure to be flattened with at least about 75 percent of the surface area of one wall in contact with the other wall with only a minimum layer of lubricant between the walls.

Schonholtz, U.S. Pat. No. 3,633,216, issued Jan. 11, 1972, discloses a rubber surgical glove having an extra thickness over at least one finger to help prevent puncturing. In one embodiment, illustrated in FIG. 4, a finger of the glove contains two rubber layers with a colored liquid in between so that a puncture of one of the layers will be immediately apparent to the surgeon.

Paschal, U.S. Pat. No. 2,694,396, issued Nov. 16, 1954, discloses and claims a massaging pad formed by sewing together a pair of satin sheets in such a way that friction between the sheets is reduced (the "warp" of one sheet is disposed at a substantial angle to the "warp" of the other). Paschal also discloses a modified form of the device comprising two sheets of flexible plastic material fused or sealed together with a lubricant on the inside. The Paschal device is allegedly an aid to massagers because it reduces the friction between the massager's hands and the body part being massaged. The device does not, however, enhance the sense of touch. Instead, the device masks the sense of touch because it is made of materials which do not readily transmit touch stimuli.

SUMMARY OF THE INVENTION

The object of this invention is to provide a method of enhancing the sense of touch.

We have discovered a method of enhancing the sense of touch which comprises: (a) placing two layers of a pliable, elastic material between the fingertips and the object being touched, each layer having a thickness of about 0.002 to 0.020 inches, a modulus of elasticity at 300 percent elongation of less than about 3,500 psi, a tensile strength of greater than about 3,000 psi, and an ultimate elongation of greater than about 300 percent so that the layers are resistant to tearing and puncturing and are able to conform to the contours of the object being touched and to readily transmit touch stimuli; (b) employing means to maintain the coefficient of kinetic friction between the two layers at less than the coefficient between the fingertips and the top layer and less than the coefficient between the object being touched and the bottom layer so that the top layer moves with the fingertips while the bottom layer remains stationary over the object being touched; and (c) moving the fingertips over the object being touched separated by the two layers of material.

This method improves the sense of touch and can be practiced in virtually any situation where the enhancement of the sense of touch is desirable. The method requires no drugs or other internal agents and the materials used to practice the method are non-toxic, reuseable, inexpensive, and readily available.

DETAILED DESCRIPTION OF THE INVENTION

This invention is based on the discovery that the sense of touch is enhanced, rather than diminished, when two layers of a pliable, elastic material with little friction between them are placed between the fingertips and the object being touched. The fingertips are then used to examine the object just as if the layers were not present. The bottom layer of material (the one in contact with the object being touched) generally remains stationary while the top layer of material (the one in contact with the fingertips) moves with the fingertips. For what is believed to be a number of reasons, the touch stimuli used to determine shape and hardness are enhanced when this method is practiced.

The two layers are made of materials (which may be the same or different) which readily transmit the desired touch stimuli through two such layers and yet are strong enough to resist tearing or puncturing. The ability of a material to transmit touch stimuli is believed to be primarily a function of its thickness and its ability to conform to the contours of the object being touched. This ability to conform is, in turn, primarily a function of the material's pliability and elasticity. In summary, the properties desired for the enclosure material are strength, pliability, and elasticity.

The material has a tensile strength of greater than about 3,000 psi, preferably greater than about 4,000 psi, and most preferably greater than about 5,000 psi. The material has a thickness of about 0.002 to 0.020 inches. At this thickness, and with a tensile strength of greater than about 3,000 psi, the material is strong enough to resist tearing or puncturing and yet thin enough to readily transmit touch stimuli. The material preferably has a thickness of about 0.003 to 0.010 inches.

The pliability of a material can be measured in terms of its modulus of elasticity. Modulus of elasticity is the force required to stretch a material a given amount. For use in this invention, a material has a modulus of elasticity at 300 percent of less than about 3,500 psi, preferably less than about 2,500 psi, and most preferably less than about 1,500 psi.

The material preferably has sufficient elasticity so that it can be stretched to at least four times its length without breaking. In other words, it is preferred that the material have an ultimate elongation of greater than 300 percent. It is more preferred that the ultimate elongation exceed 400 percent and most preferred that it exceed 500 percent.

The material has a uniformly smooth surface on each side so that minute protrusions, such as those present in a woven material, do not interfere with the sense of touch and so that low-friction movement of one layer across the other layer is facilitated.

Materials exhibiting the above-described properties of strength, pliability, elasticity, and smoothness are generally members of the class of polymers known as elastomers. Both synthetic and natural elastomers are suitable. Synthetic elastomers include certain polychloroprene polymers, butadiene-styrene copolymers, butadiene-acrylonitrile copolymers, and polyurethane polymers. A preferred polyurethane polymer is Type TF-840 polyurethane film, a commercial product of the Lord Corporation, Erie, Pennsylvania, which exhibits a modulus of elasticity at 300 percent elongation of 2,500 psi, a tensile strength of 8,500 psi, and an ultimate elongation of 500 percent. A highly preferred natural elastomer is natural rubber latex derived from the tree Hevea Braziliensis. Natural rubber latex is the most preferred material because it generally exhibits superior properties of strength, pliability, and elasticity. For example, natural rubber latexes often exhibit a modulus of elasticity at 300 percent elongation of less than 700 psi, a tensile strength of greater than 4,000 psi, and an ultimate elongation of greater than 600 percent.

It is important that there be little friction between the two layers of material so that the top layer moves with the fingertips while the bottom layer remains stationary over the object being touched. Quantitatively this means that the coefficient of kinetic friction between the two layers is less than the coefficient between the fingertips and the top layer and less than the coefficient between the object being touched and the bottom layer. Some materials exhibit this property naturally, but it is preferred to employ a liquid lubricant between the two layers to ease the movement of the top layer across the stationary bottom layer. The lubricant generally has sufficient lubricity to reduce the coefficient of kinetic friction between the layers by at least about 60 percent. The lubricant further has substantial inertness towards the layers of material. For example, petroleum fractions and animal and vegetable oils are generally unsatisfactory because they tend to dissolve many suitable elastomers, especially natural rubber latex. Suitable lubricants include mixtures of water and soap, glycerine, propylene glycol, polyoxyethylene (also known as polyethylene glycol), and silicone-based lubricants such as polydimethylsiloxane. The most preferred lubricant is Organosilicone Fluid L-45, a polydimethylsiloxane fluid which is a commercial product of the Union Carbide Corporation, Danbury, Conn.

The method of this invention may be practiced using a variety of shapes and arrangement of layers of material and lubricant. For example, two separate sheets of material with a lubricant between them are suitable. Another alternative is to employ a glove or finger covering with a sheet of material lubricated on the upper side. However, these techniques are handicapped by the presence of unenclosed lubricant. Unenclosed lubricant can spill on clothing or on furniture and can interfere with the method itself if it gets on the wrong sides of the layers of material or on the fingertips of the user. Accordingly, it is preferred that the method be practiced with a pad consisting of lubricant enclosed within two layers of material. The shape and size of the pad are not critical. The pad may be large or small depending upon the object to be touched and it may be round, square, or even shaped and worn like a glove if desired. For breast examination, a round enclosure having a diameter of about 9 inches is preferred because it fully covers and conforms to the shape of the breast.

If an enclosed pad is used, it may be formed of one or more pieces of material. For example, a suitable pad is made of two pieces of Type TF-840 polyurethane polymer heatfused together along the outside edges. However, the presence of a seam of any type tends to interfere with the movement of the pad during use. Furthermore, natural rubber latex cannot be heat- or chemically-sealed. Accordingly, it is preferred that a pad with an enclosure of a single piece of material be used. When the pad is made of natural rubber latex, a preferred enclosure has the general shape and appearance of a toy balloon with a single opening physically sealed to prevent the flow of liquid or gas therethrough. Suitable physical seals are clamps, bands, and the like.

The liquid lubricant in an enclosed pad is present in an amount large enough to fully coat the interior of the enclosure and yet small enough that the user of the pad can examine an object with only a minimum layer of lubricant between the walls of the enclosure. The amount of the liquid lubricant preferably permits the enclosure to be flattened with at least about 75 percent of the surface area of one side in contact with the other side. As an example, about 10 to 30 ml of lubricant are preferred for use with a 9 inch diameter pad.

the ease with which a pad is used is improved somewhat if a volume of gas is also present inside the enclosure. The gas has substantial inertness towards the enclosure and is preferably air for ease of manufacture. The volume of gas is generally at least about double the volume of the liquid lubricant. The combined volumes of the liquid lubricant and the gas permit the enclosure to be flattened with at least about 75 percent of the surface area of one side in contact with the other side. In the example of the 9 inch diameter pad, about 100 to 500 ml of gas are preferred.

Optimal results are obtained when the fingertips are dry, i.e., free of any discernable amounts of liquids such as water, oils, or lotions. Liquids generally reduce the coefficient of kinetic friction between the fingertips and the top layer of material, which is undesirable. Liquids also appear to actually interfere with the reception of touch stimuli by the fingertips.

While not wishing to be bound by theory, it is believed that at least five factors contribute to the touch enhancing properties of the method of this invention. First of all, this method eliminates or masks certain touch stimuli such as temperature and texture and thereby improves the ability to detect the touch stimuli which enable the determination of shape and hardness. Secondly, the method reduces friction between the user and the object being touched. This eases the movement of the fingertips across the object and helps prevent any tendency of the fingertips to skip across a portion of the object.

Thirdly, this method helps immobilize the object being touched. A very small object, protrusion, or indentation is detected most readily by passing the fingertips across it. If the object moves with the fingertips, it is more difficult to detect. For example, it is very difficult to feel a single human hair upon a hard, smooth surface. At least part of the difficulty is because the hair tends to stick to the fingers. When this method is used, the hair is immobilized and the fingertips can be moved back and forth across the hair, enabling it to be detected.

Fourthly, the layers of material adhere to and follow the contours of objects so well that they in effect increase the size of the object for detection purposes. In the above example of human hair, the increase in the hair's diameter by several thousandths of an inch (which results when the two layers conform and adhere to the hair) creates a much larger protrusion for the fingertips to feel. Fifthly, the practicing of this method may actually increase the surface area of the fingertips in contact with an object.

We claim:

1. A method of enhancing the sense of touch which comprises:
   (a) providing two layers of a pliable, elastic material, each layer having a thickness of about 0.002 to 0.020 inches, a modulus of elasticity at 300 percent elongation of less than about 3,500 psi, a tensile strength of greater than about 3,000 psi, and an ultimate elongation of greater than about 300 percent so that the layers are resistant to tearing and puncturing and are able to conform to the contours of the object being touched and to readily transmit touch stimuli;
   (b) placing the two layers between the fingertips and the object being touched in such a way that the two layers can move freely relative to each other;
   (c) maintaining the coefficient of kinetic friction between the two layers at less than the coefficient between the fingertips and the top layer and less than the coefficient between the object being touched and the bottom layer so that the top layer moves with the fingertips while the bottom layer remains stationary over the object being touched; and
   (d) moving the fingertips over the object being touched separated by the two layers of material.

2. The method of claim 1 wherein step (c) comprises maintaining a minimum layer of lubricant between the two layers of material to maintain the coefficient of kinetic friction between the two layers at less than the coefficient between the fingertips and the top layer and less than the coefficient between the object being touched and the bottom layer so that the top layer moves with the fingertips while the bottom layer remains stationary over the object being touched.

3. The method of claim 2 wherein step (a) comprises providing two layers of a pliable, elastic material, each layer having a thickness of about 0.003 to 0.010 inches, a modulus of elasticity at 300 percent elongation of less than about 2,500 psi, a tensile strength of greater than about 4,000 psi, and an ultimate elongation of greater than about 400 percent so that the layers are resistant to tearing and puncturing and are able to conform to the contours of the object being touched and to readily transmit touch stimuli.

4. The method of claim 3 additionally comprising:
   (e) maintaining the fingertips in a dry condition throughout the method.

5. The method of claim 4 wherein step (c) further comprises reducing the coefficient of kinetic friction between the layers by at least about 60 percent.

* * * * *